United States Patent
Tenconi et al.

(10) Patent No.: US 6,576,790 B1
(45) Date of Patent: Jun. 10, 2003

(54) PROCESS FOR THE PREPARATION OF GABAPENTIN

(75) Inventors: Franco Tenconi, Novi Ligure (IT); Cristiana Giordani, Novi Ligure (IT); Nicola Caraccia, Novi Ligure (IT)

(73) Assignee: Bioindustria Laboratorio Italiano Medicinali S.p.A., Novi Ligure (IT)

( * ) Notice: Subject to any disclaimer, the term of this patent is extended or adjusted under 35 U.S.C. 154(b) by 0 days.

(21) Appl. No.: 09/937,378

(22) PCT Filed: Mar. 16, 2000

(86) PCT No.: PCT/EP00/02345

§ 371 (c)(1),
(2), (4) Date: Feb. 25, 2002

(87) PCT Pub. No.: WO00/58268

PCT Pub. Date: Oct. 5, 2000

(30) Foreign Application Priority Data

Mar. 26, 1999 (IT) .......................... MI99A0625

(51) Int. Cl.⁷ ...................... C07C 229/00; C07C 227/00
(52) U.S. Cl. ......................... 562/507; 562/554
(58) Field of Search ................... 562/507, 554

(56) References Cited

U.S. PATENT DOCUMENTS 4,024,175 A    5/1977   Satzinger et al.
4,960,931 A  * 10/1990  Butler et al.
5,491,259 A  *  2/1996  Grierson et al.

FOREIGN PATENT DOCUMENTS

EP    0 340 677      11/1989
WO    WO 98/28255    7/1998

* cited by examiner

Primary Examiner—Samuel Barts
Assistant Examiner—Paul A. Zucker
(74) Attorney, Agent, or Firm—Young & Thompson

(57) ABSTRACT

A process for the preparation of gabapentin starting from gabapentin hydrochloride, which comprises the following steps: preparing a gabapentin hydrochloride aqueous solution; adjusting the pH of the solution to or about to gabapentin isoelectric point by addition of a basic compound comprising a monovalent anion; diafiltering the solution through a membrane highly selective for organic compounds with molecular weight higher than 150 and poorly selective for inorganic monovalent ions, to separate the solution into an aqueous permeate containing chloride ions and a retentate containing unsalified gabapentin substantially free from chloride ions; concentrating the retentate by increasing the pressure exerted on the membrane to obtain a concentration of unsalified gabapentin in the retentate not lower than 5%; evaporating the retentate under reduced pressure and at $T°<35°$; precipitating gabapentin by addition of an alcohol.

8 Claims, No Drawings

PROCESS FOR THE PREPARATION OF GABAPENTIN

This application is a 371 of PCT/EP00/02345 filed on Mar. 16, 1999.

The present invention generally relates to the pharmaceutical chemistry field.

More particularly, the invention relates to process for the preparation of 1-(aminomethyl)-1-cyclohexaneacetic acid, also known under the name gabapentin, having the following chemical structure:

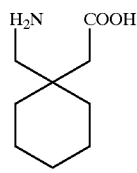

Gabapentin is an active ingredient used in the treatment of various cerebral diseases, such as epilepsy, hypokinesia, cranial traumas and the like and is the object of U.S. Pat. No. 4,024,175 and U.S. Pat. No. 4,087,544.

A number of processes for preparation of gabapentin are reported in literature; U.S. Pat. No. 4,024,175, for example, discloses some preparation methods starting from cyclohexyl-1,1-diacetic acid.

All the prior art processes yield, however, gabapentin hydrochloride, which has then to be transformed into the free amino acid by treatment with a basic ion exchanger followed by crystallization from an ethanol/ether mixture.

U.S. Pat. No. 4,894,476 discloses a process for the transformation of gabapentin hydrochloride into the free amino acid, which comprises passing an hydrochloride aqueous solution on a ion exchange resin column with use of large water volumes.

Due to the high water solubility of unsalified gabapentin, large water volumes have to be evaporated off in order to recover said compound, operating at low temperatures to prevent the formation of lactams. This makes said process hardly convenient from the industrial point of view.

Alternative methods have been suggested to overcome said drawbacks, which methods avoid the formation of the hydrochloride or any other salt. Examples of said methods can be found in U.S. Pat. No. 5,132,451, U.S. Pat. No. 5,095,148 e U.S. Pat. No. 5,068,413 and they comprise the formation of a cyanic derivative, which is then hydrogenated under drastic conditions to give the free amino acid.

These methods, however, involve the use of hydrocyanic acid derivatives, which makes them industrially impractical.

In a recent patent application, WO-A-98/28255, a novel process for the preparation of the gabapentin starting from the corresponding hydrochloride is described, which allows to solve the problems of the prior art processes, in particular U.S. Pat. No. 4,894,476, connected with the need for evaporating large water volumes at low temperatures to recover free gabapentin.

Said process comprises the following steps:
  liberation of gabapentin hydrochloride from inorganic salts from the synthesis, by solubilization of gabapentin hydrochloride in organic solvents in which the inorganic salts are insoluble, followed by filtration and evaporation of the solvent;
  displacement of HCl with amines, such as tributylamine, triethylamine and the like, in a solvent in which the hydrochlorides of said amines are soluble but free gabapentin is not soluble, which therefore precipitates in the crystalline form III;
  conversion of gabapentin form III into gabapentin form II.

The present invention aims at providing a process for the preparation of free gabapentin starting from gabapentin hydrochloride, which would overcome the drawbacks mentioned above connected with the process of U.S. Pat. No. 4,894,476, according to alternative procedures to those suggested in WO-A-98/28255.

Said problem is solved, according to the invention, by a process which comprises the steps of:
  preparing a gabapentin hydrochloride aqueous solution;
  adjusting the pH of said solution to or about to gabapentin isoelectric point by addition of a basic compound comprising a monovalent anion;
  diafiltering said solution through a membrane highly selective for organic compounds with molecular weight higher than 150 and poorly selective for inorganic monovalent ions, to separate said solution into an aqueous permeate containing chloride ions and a retentate containing unsalified gabapentin substantially free from chloride ions;
  concentrating said retentate by increasing the pressure exerted on said membrane to obtain a concentration of unsalified gabapentin in the retentate not lower than 5%;
  evaporating the retentate under reduced pressure and at $T°<35°$;
  precipitating gabapentin by addition of an alcohol.

The process according to the invention conveniently comprises a further crystallization step of the precipitated unsalified gabapentin with methanol.

The above basic compound is preferably selected from the group consisting of alkali metal and ammonium hydroxides.

The pH of the starting aqueous solution is preferably adjusted to 7.14.

During the diafiltration step, the pressure exerted on the membrane is 10–16 bars, preferably 14–15 bars.

During the concentration step, the concentration of unsalified gabapentin in the retentate is preferably brought to an about 8–10% w/v value. During said concentration step, pressure increases gradually to reach a value of about 18–22 bars.

During the diafiltration and of concentration steps, temperature is preferably kept below 25° C.

The diafiltration step is preferably carried out with the aid of nanofiltration multilayer composite membranes, such as those sold by PERMEARE S.r.l. (Italy), in particular the membrane named ACN2540HS. Such are membranes have a rejection rate of inorganic salts lower than or equal to 50% and a rejection rate of organic molecules higher than or equal to 96%. Suitable composite membranes have a thin polyamide material coating as the active layer. Other suitable membranes for the process of the invention are those made of polysulfonic resins, nylon, cellulose acetate, polypropylene and polyvinylydene fluoride (PVDF).

The process according to the invention solves the problems mentioned above with reference to the prior art processes based on the use of ion exchange resins, by means of a simple technique which requires no drastic operative conditions, such as high temperatures, which would cause the undesired formation of the gabapentin lactam.

Further advantages of the process of the invention will be more evident from the following examples.

EXAMPLE 1

5 kg of 1-(aminomethyl)-1-cyclohexaneacetic acid.HCl are dissolved in 10 volumes of deionized water at room temperature. This solution is slowly added with about 24 l of 1 M NaOH to reach pH 7.14 (gabapentin isoelectric point), while cooling to keep the temperature not above 20° C.

The resulting solution is subjected to diafiltration, at a temperature of about 22° C., in an about 100 l pilot plant, using a nanofiltration multilayer composite membrane PMFARE ACN2540HS, having high selectivity for organic compounds with molecular weight higher than 150 (rejection rate higher than or equal to 98%) and low selectivity to inorganic monovalent ions (50% rejection rate).

The pressure exerted on the membrane is about 14 bars and the outlet pressure is about 12 bars.

The permeate is added with deionized water dosing the NaCl in the permeate.

Values remain almost steady in the first amounts of permeate, then decrease again. The permeate flow rate is fixed at about 60 l/h. After 4 hours the NaCl in the permeate is 98% on the calculated content. At this point the concentration step is started. Productivity remains high and the pressure increase observed in this step (the inlet pressure is up to about 22 bars and the outlet one to about 20 bars) to keep the permeate flow rate steady is due to an increase in the osmotic pressure following the increase in the solute concentration. When an about 50 l volume is reached, the retentate solution containing about 10% unsalified gabapentin is recovered. Finally the solution is evaporated under reduced pressure and at a temperature<35° C., reducing the volume from 50 to 10 l, and gabapentin is precipitated by addition of isopropyl alcohol. The precipitated solid is finally recovered by filtration and crystallized from methanol, to obtain 3.3 kg of pure gabapentin.

EXAMPLE 2

5 kg of 1-(aminomethyl)-1-cyclohexaneacetic acid HCl are dissolved in 10 volumes of deionized water at room temperature. This solution is slowly added with about 24 l of 1 M KOH to reach pH 7.14 (gabapentin isoelectric point), while cooling to keep the temperature not above 20° C.

The resulting solution is subjected to diafiltration, at a temperature of about 22° C., in the same pilot plant as above, using the membrane PERMEARE ACN2540HS. The pressure exerted on the membrane is about 14 bars and the outlet pressure is about 12 bars.

The permeate is added with deionized water dosing the KCl in the permeate.

Values remain almost steady in the first amounts of permeate, then decrease again. The permeate flow rate is fixed at about 55 l/h. After 4 hours, the KCl in the permeate is 98% on the calculated content. At this point the concentration step is started, increasing the inlet pressure to about 22 bars. When an about 50 l volume is reached, the retentate solution containing about 10% unsalified gabapentin is recovered and the same operations as in example 1 are carried out, to obtain 3.25 kg of crystalline unsalified gabapentin.

EXAMPLE 3

5 kg of 1-(aminomethyl)-1-cyclohexaneacetic acid HCl are dissolved in 10 volumes of deionized water at room temperature. This solution is slowly added with about 24 l of 1 M $NH_4OH$ to reach pH 7.14 (gabapentin isoelectric point), while cooling to keep the temperature not above 20° C.

The resulting solution is subjected to diafiltration, at a temperature of about 20° C., in the same pilot plant as above, using the membrane PERMEARE ACN2540HS. The pressure exerted on the membrane is about 14 bars and the outlet pressure is about 12 bars.

The permeate is added with deionized water dosing the $NH_4Cl$ in the permeate.

The flow rate of the permeate is fixed at about 65 l/h. After 4 hours the $NH_4Cl$ in the permeate is 98% on the calculated content. At this point the concentration step is started, increasing the inlet pressure to about 22 bars. When an about 50 l volume is reached, the retentate solution containing 10% unsalified gabapentin is recovered and the same operations as in example 1 are carried out, to obtain 3.3 kg of crystalline unsalified gabapentin.

What is claimed is:

1. A process for the preparation of gabapentin starting from gabapentin hydrochloride, which comprises the following steps:

preparing a gabapentin hydrochloride aqueous solution;

adjusting the pH of said solution to or about to gabapentin isoelectric point by addition of a basic compound comprising a monovalent anion;

diafiltering said solution through a membrane highly selective for organic compounds with molecular weight higher than 150 and poorly selective for inorganic monovalent ions, to separate said solution into an aqueous permeate containing chloride ions and a retentate containing unsalified gabapentin substantially free from chloride ions;

concentrating said retentate by increasing the pressure exerted on said membrane to obtain a concentration of unsalified gabapentin in the retentate not lower than 5% evaporating the retentate under reduced pressure and at T° C.<35° C.;

precipitating gabapentin by addition of an alcohol.

2. A process as claimed in claim 1, comprising a further crystallization step of the precipitated gabapentin with methanol.

3. A process as claimed in claim 1, wherein said basic compound is selected from the group consisting of alkali metal and ammonium hydroxides.

4. A process as claimed in claim 3, wherein the pH of said aqueous solution is adjusted to 7.14.

5. A process as claimed in claim 4, wherein the concentration of unsalified gabapentin in the retentate is brought, during said concentration step, to an about 8–10% w/v value.

6. A process according to claim 1, wherein during the diafiltration and concentration steps, the temperature is kept below 25° C.

7. A process according to claim 1, wherein said membrane is a nanofiltration multilayer composite membrane having a rejection rate of organic compounds with molecular weight above 150 higher than or equal to 96%.

8. A process as claimed in claim 7, wherein said membrane comprises a layer made of polyamide, polysulfonic resins, nylon, cellulose acetate or polyvinylydene fluoride.

* * * * *